United States Patent
Binkhathlan et al.

(10) Patent No.: US 9,622,973 B1
(45) Date of Patent: Apr. 18, 2017

(54) POLY ε-CAPROLACTONE-ETHOXYLATED FATTY ACID COPOLYMERS

(71) Applicant: KING SAUD UNIVERSITY, Riyadh (SA)

(72) Inventors: Ziyad Binkhathlan, Riyadh (SA); Abdullah H. Alomrani, Riyadh (SA); Aws Alshamsan, Riyadh (SA); Ibrahim I. Aljuffali, Riyadh (SA); Raisuddin Ali, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/064,507

(22) Filed: Mar. 8, 2016

(51) Int. Cl.
C08G 63/08 (2006.01)
A61K 9/16 (2006.01)
C08G 63/664 (2006.01)

(52) U.S. Cl.
CPC .......... *A61K 9/1647* (2013.01); *A61K 9/1682* (2013.01); *C08G 63/664* (2013.01)

(58) Field of Classification Search
CPC .................................................. C08G 63/08
See application file for complete search history.

(56) References Cited

U.S. PATENT DOCUMENTS

| | | | |
|---|---|---|---|
| 7,141,643 | B2 | 11/2006 | Dixon et al. |
| 9,168,221 | B2 * | 10/2015 | de Leeuw ............ A61K 9/0024 |
| 2010/0092425 | A1 * | 4/2010 | von Andrian .......... A61K 39/00 424/85.2 |

OTHER PUBLICATIONS

Nanaki et al., "Synthesis of biocompatible poly(ε-caprolactone)-block-poly(propylene adipate) copolymers appropriate for drug nanoencapsulation in the form of core-shell nanoparticles" Int. J. Nanomedicine, 2011, vol. 6, 2981-2995.

* cited by examiner

*Primary Examiner* — Rachel Kahn
(74) *Attorney, Agent, or Firm* — Richard C. Litman

(57) ABSTRACT

A block copolymer comprising ε-caprolactone units and polyoxyethylene stearate units, wherein the block copolymer has the following formula:

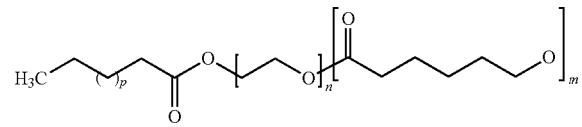

wherein n, m, and p are integers greater than 0. The block copolymer is prepared by polymerizing (i) ε-caprolactone and (ii) polyoxyethylene stearate in the presence of a catalyst such as stannous octoate.

10 Claims, 8 Drawing Sheets

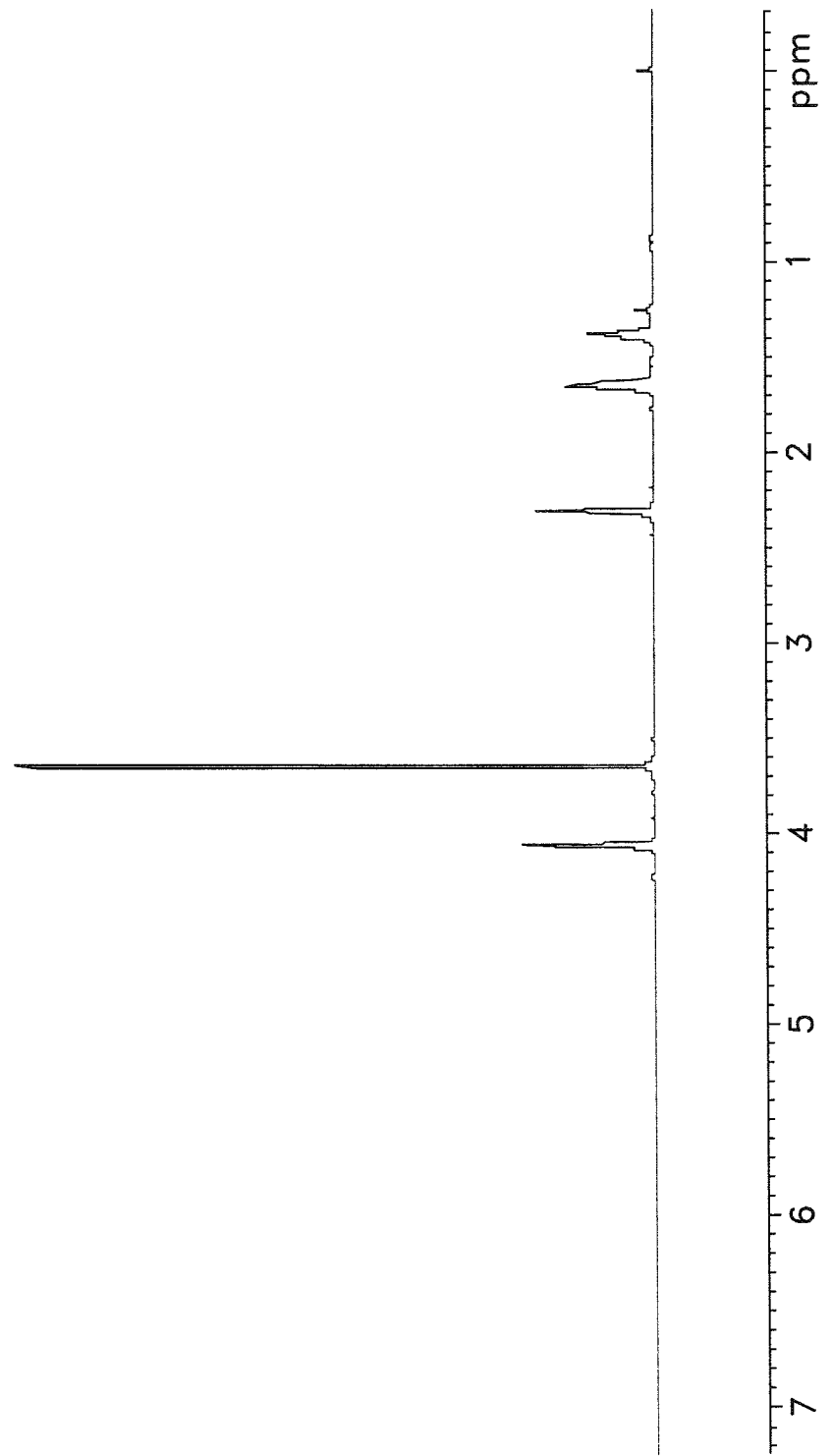

POLY ε-CAPROLACTONE-ETHOXYLATED FATTY ACID COPOLYMERS

BACKGROUND OF THE INVENTION

1. Field of the Invention

The present invention relates to polymers, and particularly to nanocarrier-forming poly(ε-caprolactone)-poly ethoxylated fatty acid block copolymers.

2. Description of the Related Art

Ethoxylated fatty acids that are sold under the trademark Myrj™ are non-ionic surfactants widely used with various drug delivery systems. The presence of PEG (poly ethylene glycol) in the molecule extends the circulation time of the drug in plasma, while fatty acid enhances the solubility of the fat-soluble drug. Several derivatives of these ethoxylated fatty acids with different PEG chain lengths have been studied. Depending on the length of PEG used, the ethoxylated fatty acid products have hydrophilic-lipophilic balance (HLB) values in the range of 11-18.8 and critical micelle concentrations (CMC) in the micro molar range.

The US FDA has approved the ethoxylated fatty acids sold under the trademark Myrj™ as safe pharmaceutical excipients used in drug formulation and food additives. In recent years, the ethoxylated fatty acids have been extensively used in the pharmaceutical industry. Several of these ethoxylated fatty acid products have been used as absorption enhancers, emulsifiers, solubilizers, permeation enhancers and stabilizers. Some derivatives of these ethoxylated fatty acids have also been used as inhibitors of P-gp (p-glycoprotein) to increase the oral bioavailability of P-gp substrates.

Poly(ε-Caprolactone) (PCL) is a biodegradable and biocompatible polyester that has been extensively studied for controlled drug delivery and tissue engineering applications. It has the advantage of being compatible with a wide range of drugs, which allows homogenous drug distribution in the polymer matrix. Moreover, PCL exhibit a long degradation time leading to sustained drug release that could last for months. PCL has flexible mechanical properties that are suitable for medical applications including drug delivery. Compared to other core-forming blocks in the poly(ester) category, such as PLGA (poly(lactic-co-glycolic acid)) and PLA (poly D-lactic acid), PCL is more hydrophobic, which makes it more compatible with hydrophobic drugs. The hydrophobicity of PCL has pushed the CMC of PEG-b-PCL to extremely low concentration in 100 nM range. PCL-based polymeric micelles have been successfully used to deliver a variety of lipophilic drugs including P-gp inhibitors such as Cyclosporine A and valspodar and some of the chemotherapeutic agents such as doxorubicin and paclitaxel. Thus, PCL is an important synthetic biomedical material with controlled biodegradability, which has already been approved by US FDA and European Medicines Agency (EMA) for clinical use as implants/drug delivery system.

Thus, biodegradable block copolymers for use in drug delivery systems are desired.

SUMMARY OF THE INVENTION

The poly ε-caprolactone-ethoxylated fatty acid copolymers can be block copolymers including: ε-caprolactone units and ethoxylated fatty acid units. The copolymers can include compounds of Formula I, as shown below:

$$H_3C\text{―}(\text{―})_p\text{―}C(=O)\text{―}O\text{―}[CH_2CH_2O]_n\text{―}[C(=O)(CH_2)_5O]_m \quad I$$

wherein n, m and p are integers greater than 0.

These and other features of the present invention will become readily apparent upon further review of the following specification and drawings.

BRIEF DESCRIPTION OF THE DRAWINGS

FIG. 2B is a representative 1H-NMR spectra of PCL88-Myrj™-S100 block copolymer.

Similar reference characters denote corresponding features consistently throughout the attached drawings.

DETAILED DESCRIPTION OF THE PREFERRED EMBODIMENTS

The poly ε-caprolactone-ethoxylated fatty acid copolymers can be block copolymers including: ε-caprolactone units and ethoxylated fatty acid units. For example, the copolymers can be block copolymers including: ε-caprolactone units and polyoxyethylene stearate units, e.g., polyoxyethylene monostearate units. The copolymers can include compounds of Formula I, as shown below:

$$H_3C\text{―}(\text{―})_p\text{―}C(=O)\text{―}O\text{―}[CH_2CH_2O]_n\text{―}[C(=O)(CH_2)_5O]_m \quad I$$

wherein n, m and p are integers greater than 0.

According to an embodiment, n can be from 1 to 100, m can be from 10 to 100, and p can be from 10-18. For example, p can be 14 or 15. The block copolymer can possess an average molecular weight of at least 1500 Daltons or greater, preferably 1500 to 50,000 Daltons.

In an exemplary embodiment, the block copolymer is prepared by polymerizing (i) ε-caprolactone and (ii) polyoxyethylene stearate in the presence of a catalyst, wherein the polymerization reaction occurs at a temperature of about 140° C. for about 4 hours and wherein the catalyst is stannous octoate.

The copolymers of Formula I can be prepared by polymerizing (i) ε-caprolactone and (ii) polyoxyethylene stearate in the presence of a catalyst. The catalyst can be stannous octoate. For example, ethoxylated fatty acids sold under the trademark of Myrj™, ε-caprolactone, and stannous octoate or bidentate sulfonamide zinc ethyl complex can be added to a previously flamed ampoule, purged with nitrogen, and sealed under vacuum. The polymerization reaction can be conducted at a temperature of about 140° C. for about 4 hours to about 5 hours. The reaction can be terminated by cooling the product to room temperature. The produced block copolymer of Formula I typically has a molecular weight in the range of about 1500 Daltons to about 50,000 Daltons or higher.

Figure 1:
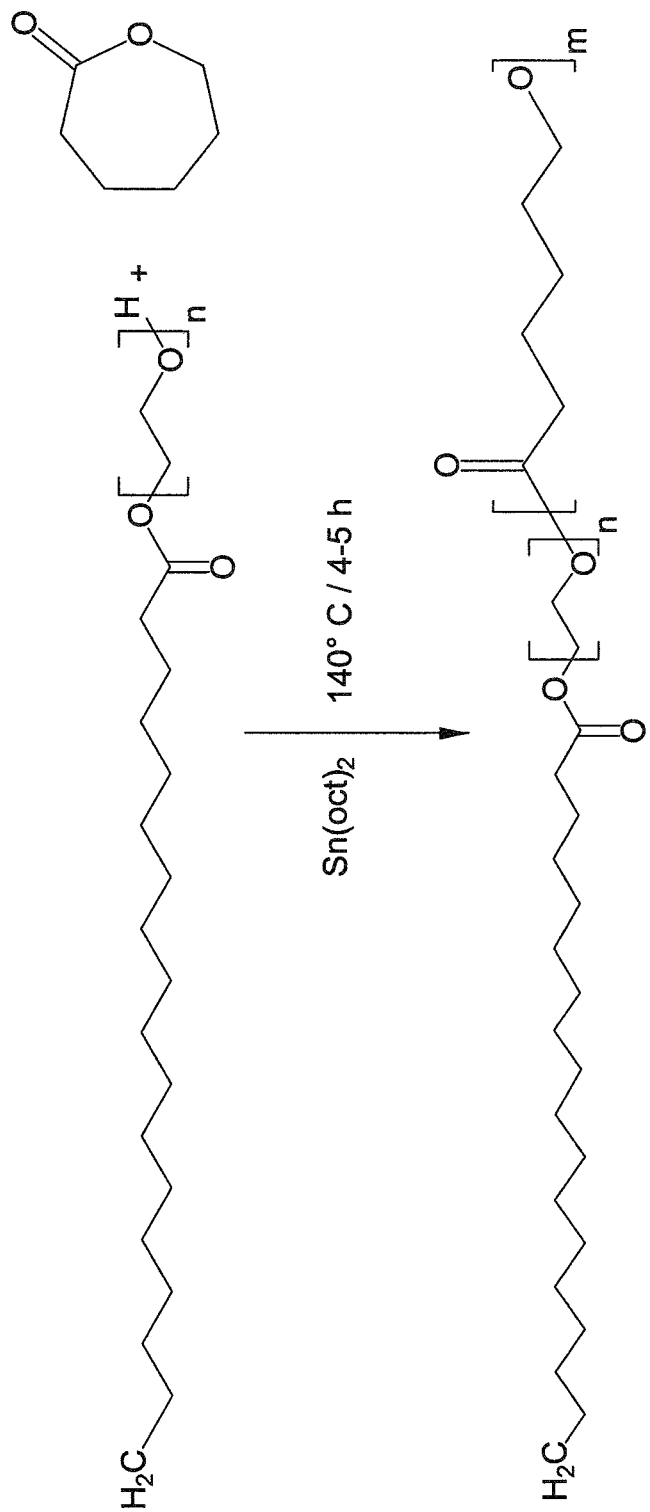
FIG. 1 is an exemplary procedure for creating the PCL-ethoxylated fatty acid block copolymers.

In an exemplary embodiment, the PCL-Myrj™ copolymer with various PCL/Myrj™ ratios were synthesized by ring opening bulk polymerization of ε-caprolactone using Myrj™ as an initiator and stannous octoate as a catalyst as depicted schematically in FIG. 1.

The copolymers of Formula I are biodegradable and can be used for drug delivery. For example, self-assembled nanocarriers including the copolymers of Formula I can be prepared by dissolving a block copolymer of Formula I in an organic solvent to form a solution; adding the solution drop-wise into distilled water and evaporating the organic solvent to form self-assembled nanocarriers. The nanocarriers can have a mean diameter of about 60 nm to about 100 nm.

The PCL-Myrj™ copolymers described herein provide numerous advantages. For example, these copolymers improve the kinetic and thermodynamic stability of the micelles formed by reducing the CMC and therefore, the micelles become more resistant to dilution. Additionally, the PCL-Myrj™ copolymers enhance the hydrophobic drug loading capacity inside the core of the micelles and further enhance the solubility and permeability of hydrophobic drugs across cellular membranes, thereby controlling the rate of drug release from the micelles/nanocarriers. Moreover, the PCL-Myrj™ copolymers possess potential use as a targeted delivery system for drugs and diagnostic agents as well as possess potential use as a delivery system for treatment of multi-drug resistant tumors.

The following examples will further illustrate the synthetic processes of making the PCL-Myrj™ copolymers and the nanocarriers.

Example 1

Synthesis of PCL-Myrj™ Copolymers

PCL-Myrj™ copolymer with various PCL/Myrj™ ratios were synthesized by ring opening bulk polymerization of ε-caprolactone using Myrj™ as an initiator and stannous octoate as a catalyst as illustrated in FIG. 1. Other catalyst such as bidentate sulfonamide zinc ethyl complex can also be used. Myrj™, ε-caprolactone and stannous octoate were added to a previously flamed 10 mL ampoule, nitrogen purged, then sealed under vacuum. The polymerization reactions were allowed to proceed for 4-5 h at 140° C. in oven. The reaction was terminated by cooling the product to room temperature. Table 1 shows the representative list of synthesized PCL-Myrj™ copolymers.

TABLE 1

| Block copolymer[a] | Theor. MW (g/mol) | Mn (g/mol)[b] | Mn (g/mol)[c] | PDI[d] |
|---|---|---|---|---|
| PCL$_{18}$-b-Myrj ™ S40 | 4,100 | 3,500 | 4,300 | — |
| PCL$_{35}$-b-Myrj ™ S40 | 6,050 | 5,700 | 4,800 | 1.23 |
| PCL$_{44}$-b-Myrj ™ S100 | 9,700 | 9,400 | 9,000 | 1.05 |
| PCL$_{88}$-b-Myrj ™ S100 | 14,650 | 14,600 | 13,700 | 1.16 |

In Table 1, the superscript "a" represents the polymerization degree of each block determined by $^1$H NMR; the superscript "b" represents the number-average molecular weight measured by $^1$H NMR; the superscript "c" represents the number-average molecular weight measured by GPC; the superscript "d" represents the polydispersity index ($M_w/M_n$) determined by GPC. The ethoxylated fatty acid sold under the trademark Myrj™ 40, and referenced in Table 1 above, refers to polyoxyethylene (40) stearate. The ethoxylated fatty acid sold under the trademark Myrj™ S100, and referenced in Table 1 above, refers to polyoxyethylene (100) stearate.

Figure 2A:
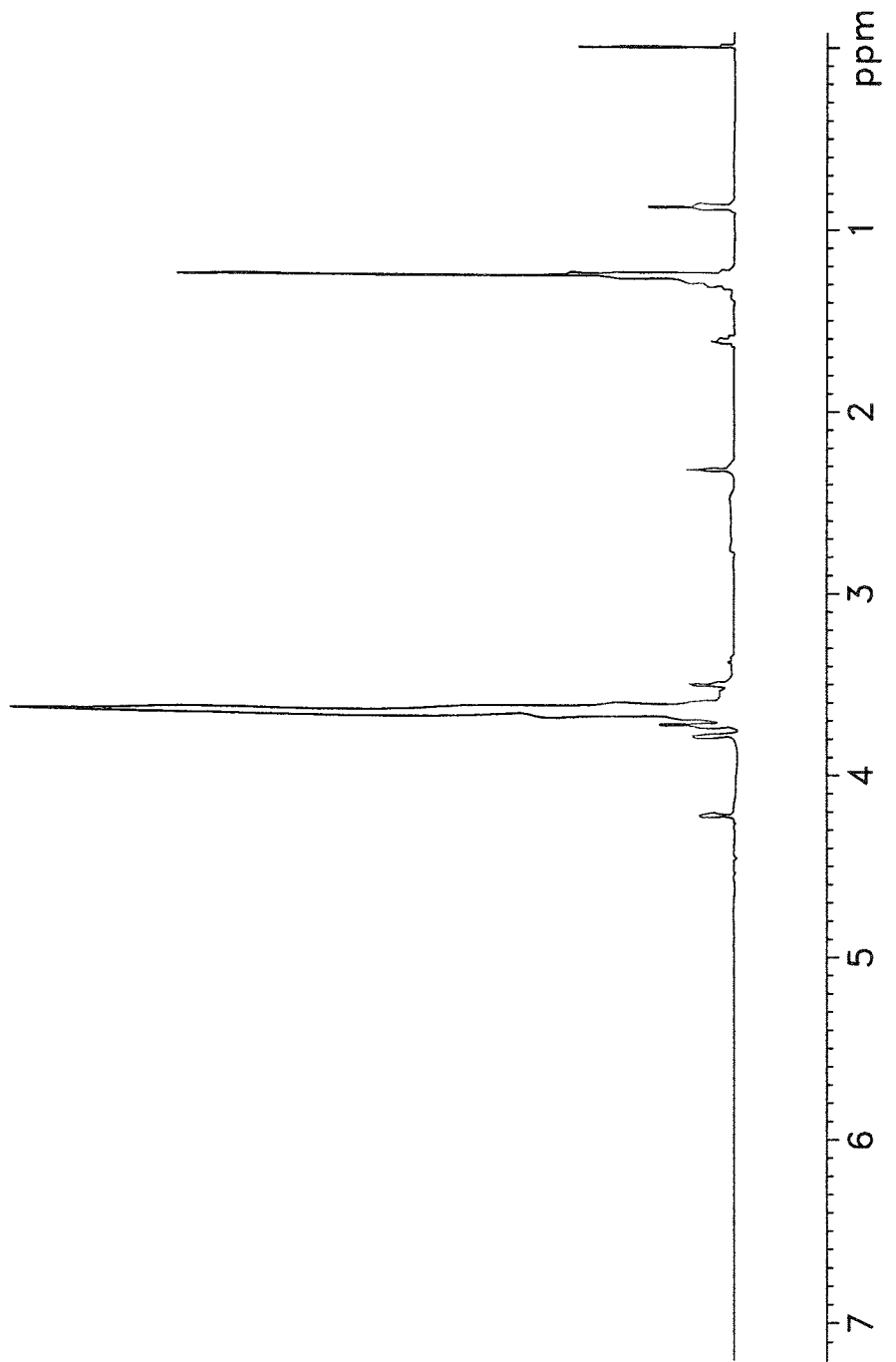
FIG. 2A is a representative 1H-NMR spectra of Myrj™ S100.

Table 1 displays the calculated Mn values of the synthesized PCL-Myrj™ copolymers. The number average molecular weight of PCL-Myrj™ copolymers formed was determined from $^1$H NMR spectrum comparing peak intensity of PEG (—CH$_2$CH$_2$O—, δ=3.65 ppm) to that of PCL (—OCH$_2$—, δ=4.07 ppm). They were calculated by using the integration area of the peaks of methylene protons of PCL and PEG at 4.07 ppm and 3.65 ppm, respectively. The calculated Mn values obtained from GPC confirmed the NMR data. The polymerization reaction yielded PCL-Myrj™ copolymers with a unimodal distribution, as confirmed by GPC. The representative $^1$H NMR spectra of Myrj™ S100 and PCL$_{88}$-Myrj™ S100 are shown in FIGS. 2A and 2B respectively.

Figure 3A:
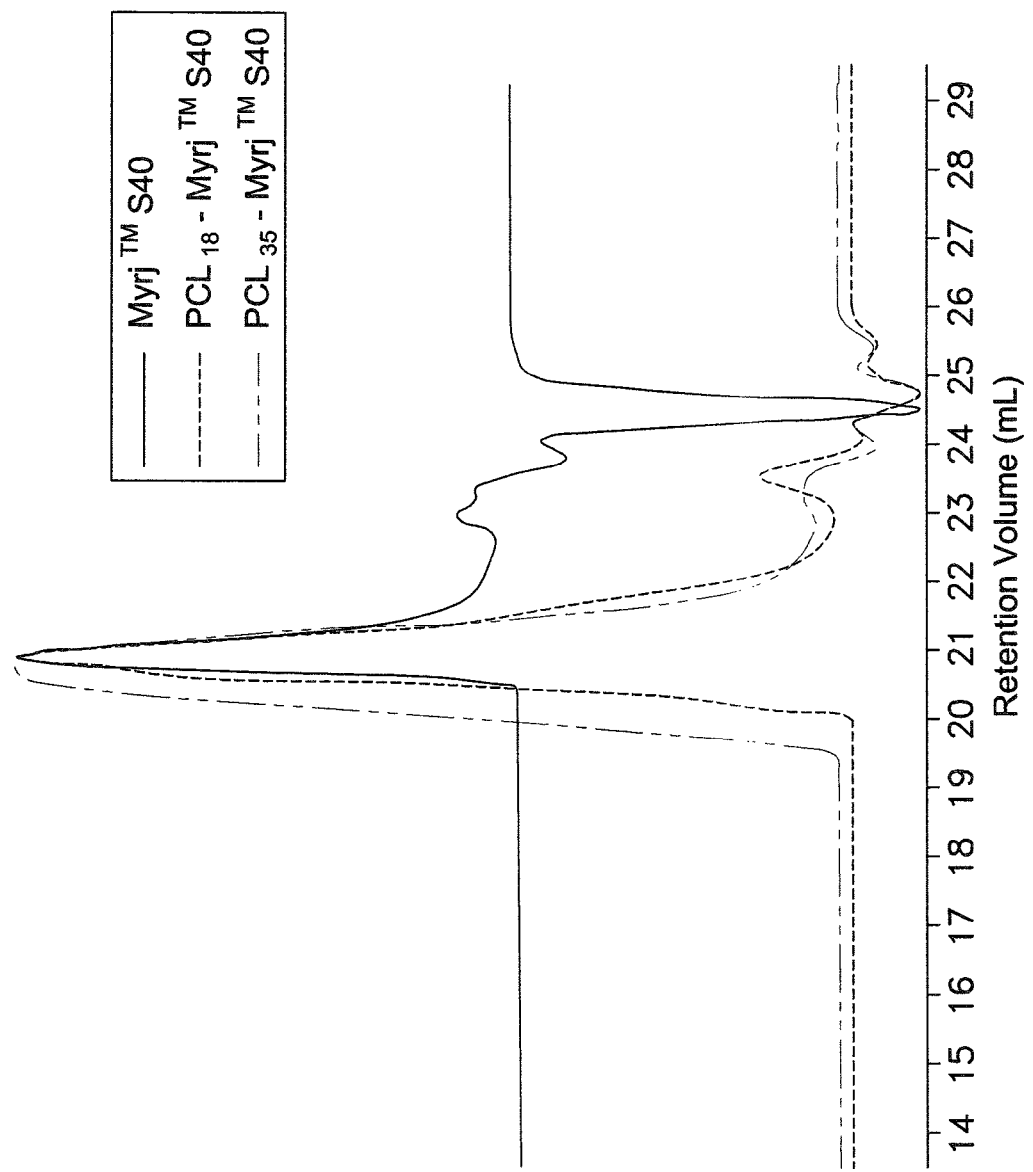
FIG. 3A is a Gel Permeation Chromatography (GPC) chromatogram of Myrj™ S40 and PCL-Myrj™ S40.
Figure 3B:
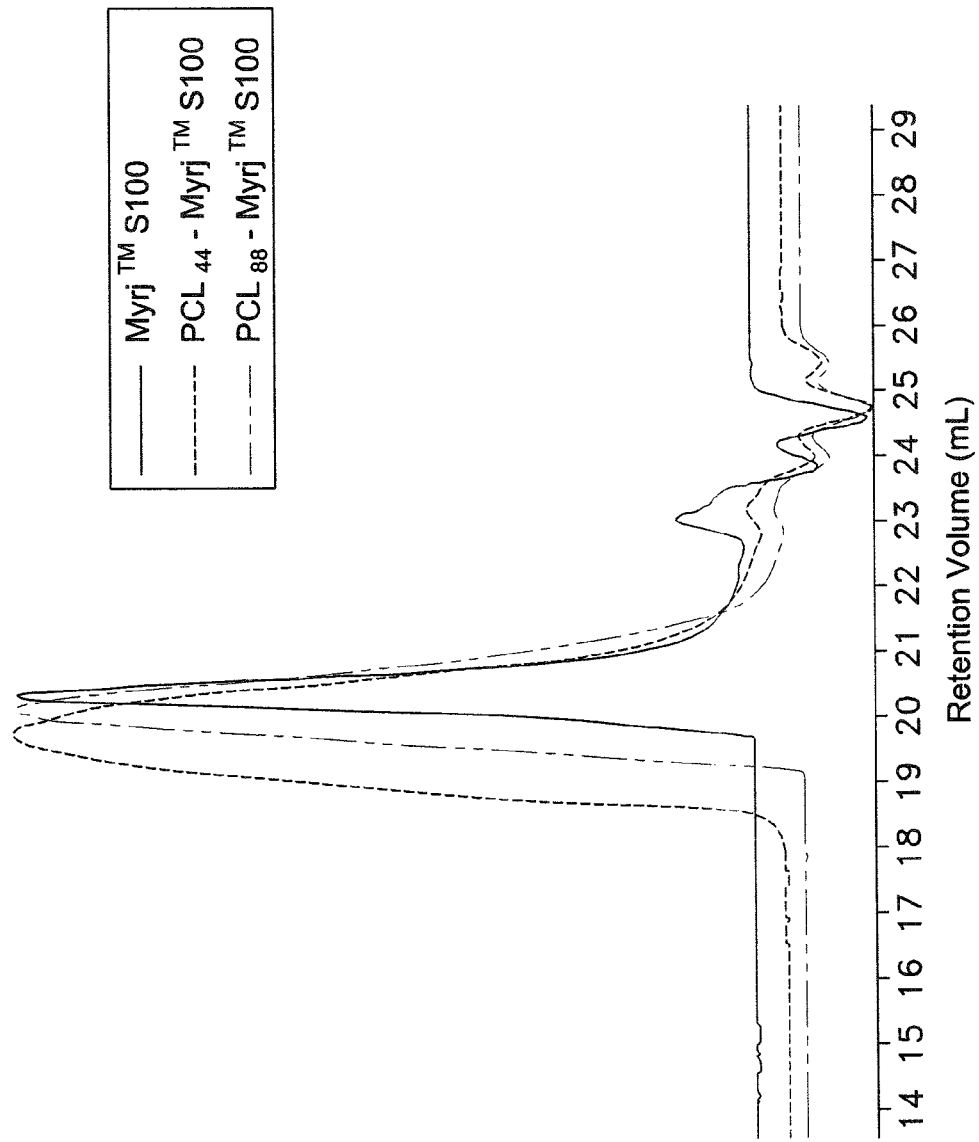
FIG. 3B is a Gel Permeation Chromatography (GPC) chromatogram of Myrj™ S100 and PCL-Myrj™ S100 block copolymers.

The weight and number average molecular weight as well as polydispersity of prepared polymers were assessed by gel permeation chromatography (GPC) (Viscotek TDA 305-040 Triple Detector Array, Viscotek Corp., Houston, Tex., USA). Samples (100 μL from 15 mg/mL polymer stock solutions in THF) were injected into an 8.0×300 mm Viscotek T6000M column (Viscotek Corp., Houston, Tex., USA) with guard column. The mobile phase was THF delivered at a flow rate of 1 ml/min. The calibration curve was established by using six polystyrene standards. GPC chromatograms of Myrj™ and PCL-Myrj™ copolymers are provided in FIGS. 3A and 3B respectively. The molecular weight of the PCL-Myrj™ copolymers was determined to be in the range of 1,570-46,500 g/mol.

Figure 4:
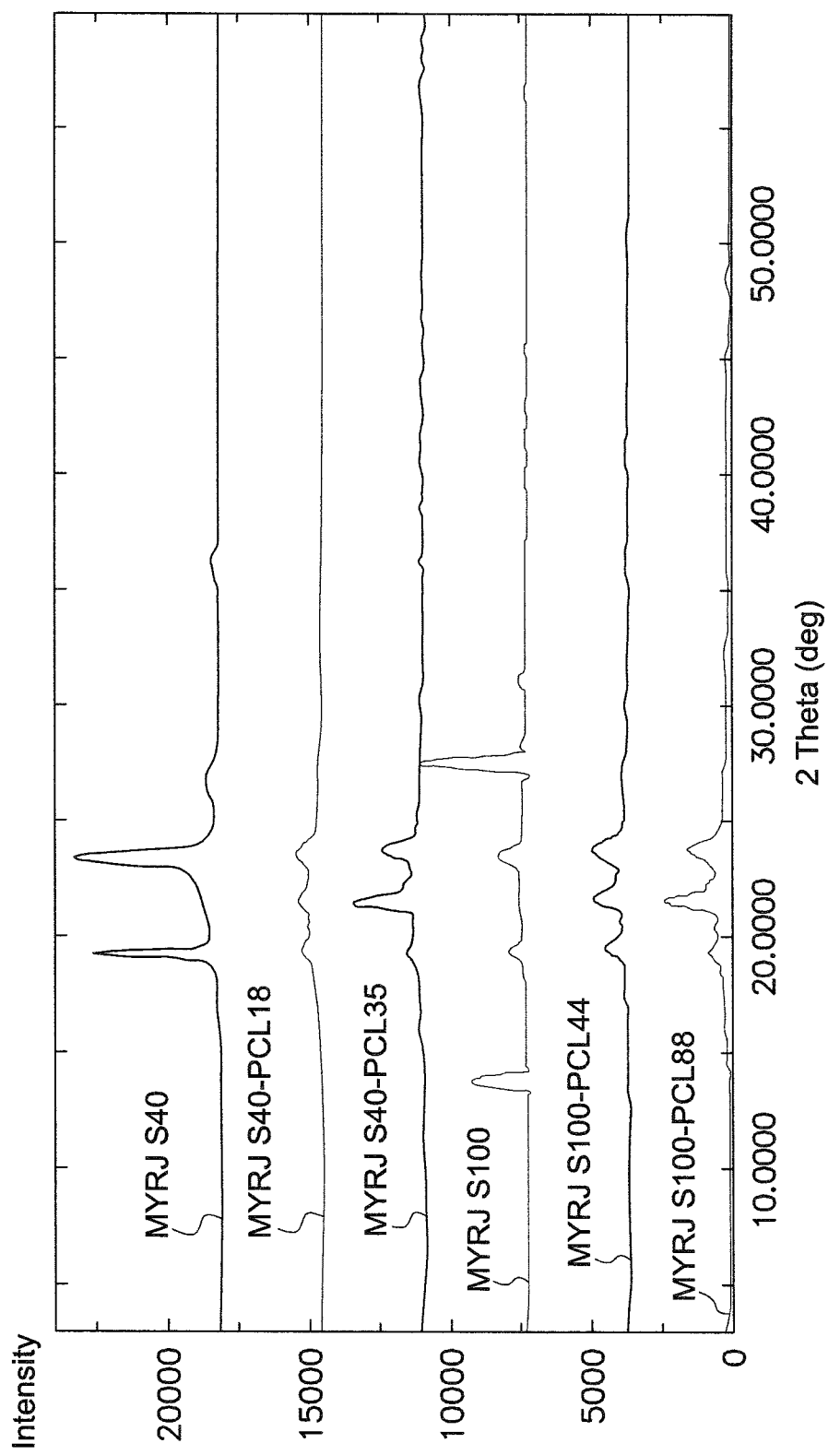
FIG. 4 shows a representative X-ray diffraction (XRD) spectra of Myrj™ and PCL-Myrj™ block copolymers.
Figure 5:
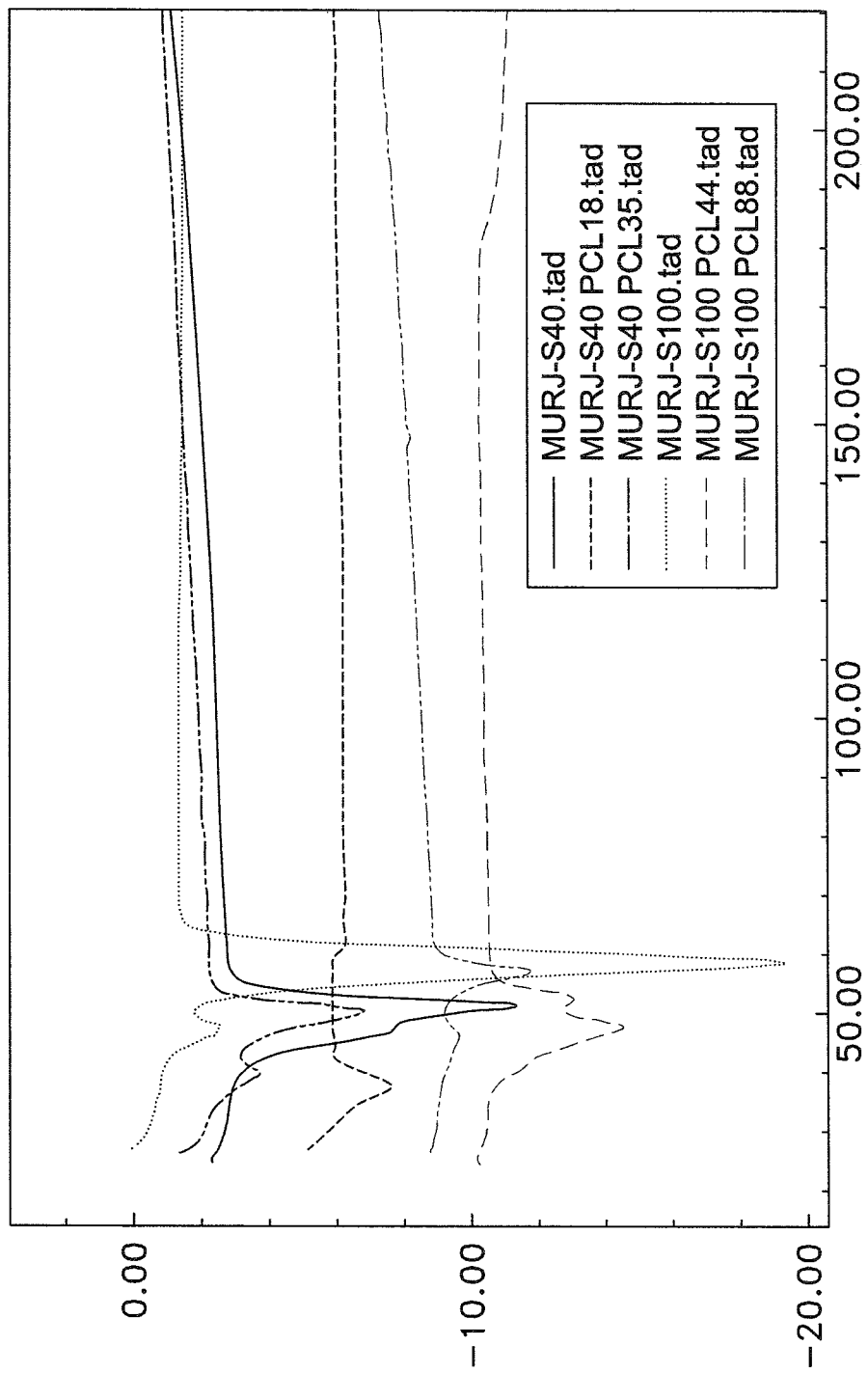
FIG. 5 is a Differential Scanning Calorimetry (DSC) thermograms of Myrj™ and PCL-Myrj™ block copolymers.
Figure 6:
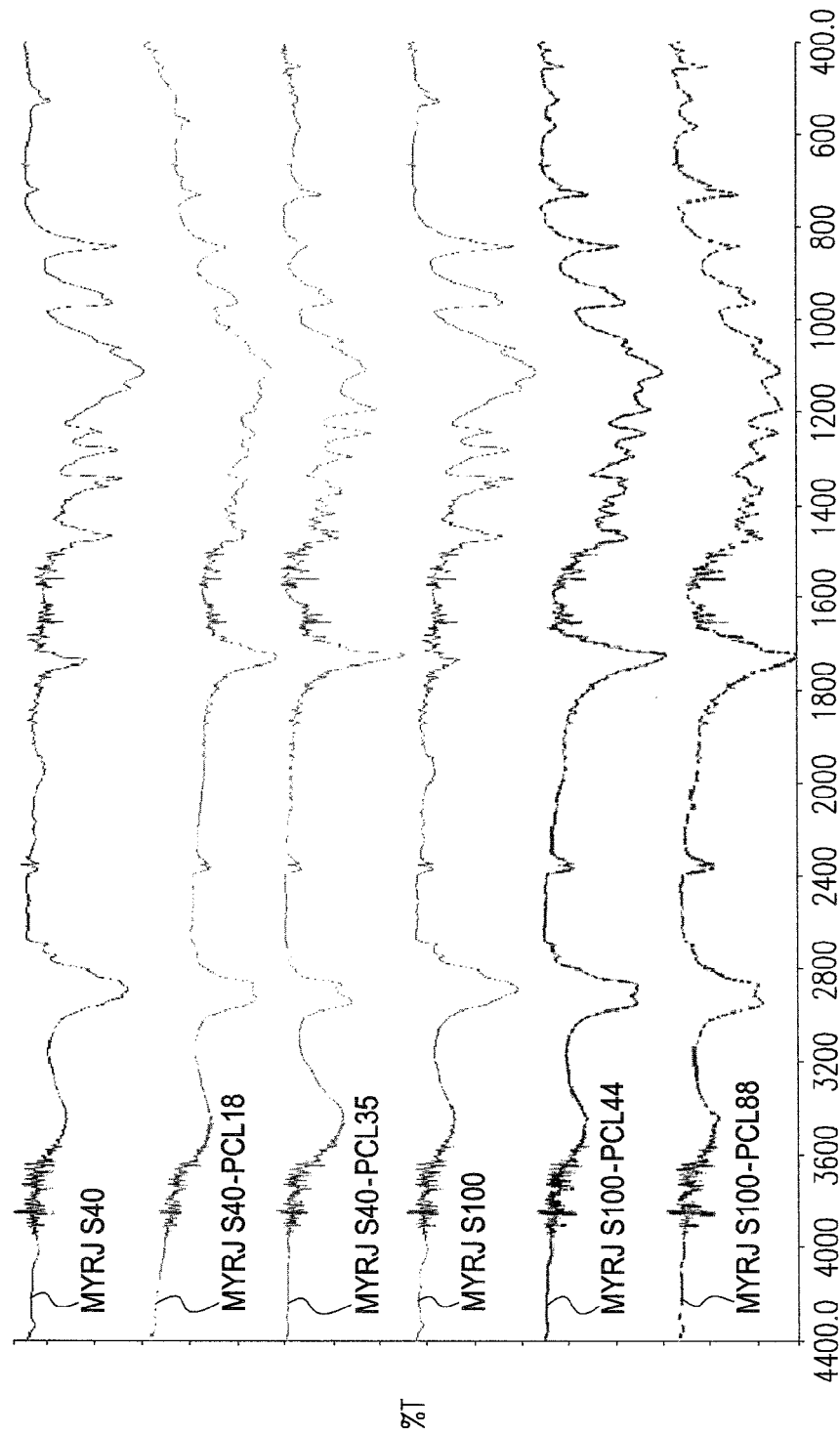
FIG. 6 is a representative FTIR spectra of Myrj™ and PCL-Myrj™ block copolymers.

X-ray Diffractometer was used to study the crystallinity state of the synthesized copolymers. Samples of the copolymers and Myrj™ were loaded in the XRD instrument (automated Rigaku Ultima IV). The X-ray diffractogram of the investigated sample was collected using 2theta (2θ) scan axis mod, scan speed set at 0.5°/min, and covering scan range of 3.0-50.0 deg. The scanning process was performed at room temperature. FIG. 4 is a representative XRD spectra of Myrj™ and PCL-Myrj™ copolymers synthesized according to the method herein described.

The thermograms of Myrj™ and PCL-Myrj™ were obtained using differential scanning calorimetry (DSC-60, Shimadzu, Japan). Sample (3-5 mg) were loaded in an aluminum pan and sealed with aluminum lids by a crimper. The sample was then thermally scanned against an empty aluminum pan with lid, at heating rate of 10° C./min, and covering temperature ranging from 25-200° C. Nitrogen purging at 40 ml/min was used during scanning. The TA-60WS thermal analysis software was used to calculate the thermal parameters of the scanned sample.

The FTIR spectra of the synthesized copolymers were obtained using an FTIR spectrophotometer (PerkinElmer, USA). Copolymer sample was ground with potassium bromide (spectroscopic grade) and compressed into a thin disk using hydraulic press before scanning from 4400 to 400 cm$^{-1}$.

Example 2

Assembly of PCL-Myrj™ Block-Copolymers

Assembly of block copolymers was achieved by co-solvent evaporation where PCL-Myrj™ (30 mg) dissolved in acetone (0.5 mL) was added in a drop-wise manner (1 drop/15 s) to stirring distilled water (3 mL). The remaining acetone was removed by evaporation at room temperature under vacuum. Mean diameter and polydispersity of self-assembled structures in aqueous media were defined by light scattering (Zetasizer™ Nano ZS, Malvern Instrument Ltd., UK). The sizes of the nanocarriers were in the range of about 60 nm to about 80 nm as shown in Table 2. The nanocarrier sizes could be less than 60 nm or greater than 80 nm. Other methods such as dialysis and film hydration can also be used to prepare the nanocarriers.

TABLE 2

| Block Copolymer[a] | Size (nm)[a] | Poly dispersity (PD[b]) |
|---|---|---|
| PCL$_{18}$-b-Myrj ™ S40 | — | — |
| PCL$_{35}$-b-Myrj ™ S40 | — | — |
| PCL$_{44}$-b-Myrj ™ S100 | 83.6 | 0.583 |
| PCL$_{88}$-b-Myrj ™ S100 | 63.2 | 0.213 |

In Table 2, the superscripts "a" and "b" represent mean diameter ($Z_{ave}$) and polydispersity of unloaded nanocarriers estimated by the DLS technique.

It is to be understood that the present invention is not limited to the embodiments described above, but encompasses any and all embodiments within the scope of the following claims.

We claim:

1. A block copolymer having the following formula:

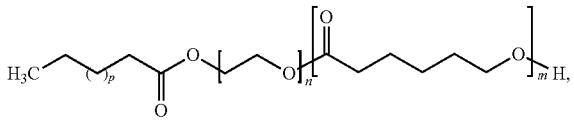

wherein n, m, and p are integers, wherein n is 1 to 100, m is 10 to 100, and p is 14.

2. The block copolymer of claim 1, wherein the block copolymer has an average molecular weight of 4000 Daltons or greater.

3. A method of preparing the block copolymer of claim 1, comprising polymerizing (i) ε-caprolactone and (ii) polyoxyethylene stearate in the presence of a catalyst.

4. The method of claim 3, wherein the polymerization reaction occurs at a temperature of about 140° C. for about 4 hours to about 5 hours.

5. The method of claim 3, wherein the catalyst comprises at least one of stannous octoate and bidentate sulfonamide zinc ethyl complex.

6. The method of claim 3, wherein: the copolymer has a molecular weight in the range of 1500 to 50,000 Daltons.

7. A method of preparing self-assembled nanocarriers comprising:
dissolving the block copolymer of claim 1 in an organic solvent to form a solution;
adding the solution drop-wise into distilled water; and
evaporating the organic solvent to form self-assembled nanocarriers.

8. The method of preparing self-assembled nanocarriers according to claim 7, wherein a mean diameter of the nanocarriers is at least 50 nm.

9. The method of preparing self-assembled nanocarriers according to claim 7, wherein a mean diameter of the nanocarriers is greater than 50 nm.

10. The method of preparing self-assembled nanocarriers according to claim 7, wherein the organic solvent comprises at least one of acetone, tetrahydrofuran, acetonitrile, and dimethyl sulfoxide.

* * * * *